United States Patent

Woo et al.

[11] Patent Number: 4,525,577
[45] Date of Patent: Jun. 25, 1985

[54] POLYMERS OF 3,3-DISUBSTITUTED-FURANDIONE COMPOUNDS

[75] Inventors: Edmund P. Woo; Michael J. Mullins, both of Midland, Mich.

[73] Assignee: The Dow Chemical Company, Midland, Mich.

[21] Appl. No.: 601,147

[22] Filed: Apr. 17, 1984

Related U.S. Application Data

[63] Continuation of Ser. No. 214,611, Dec. 9, 1980, abandoned.

[51] Int. Cl.$^3$ .............................................. C08G 73/10
[52] U.S. Cl. .................................... 528/327; 528/73; 528/310; 528/323; 528/330; 528/331; 528/335; 528/346; 528/347; 528/350
[58] Field of Search ........................................ 528/327

[56] References Cited

U.S. PATENT DOCUMENTS

| | | | |
|---|---|---|---|
| 3,642,712 | 2/1972 | Sambeth et al. | 528/327 |
| 4,093,634 | 6/1978 | Lamberti et al. | 260/346.74 |
| 4,271,288 | 6/1981 | Woo | 528/183 |

OTHER PUBLICATIONS

Barnes et al., JACS, 82, 4960, (1960), (see p. 4961, formula IX).
Campbell et al., *Macromolecules*, 8, 706, (1975).

*Primary Examiner*—Harold D. Anderson
*Attorney, Agent, or Firm*—Norman L. Sims

[57] ABSTRACT

Poly(imide)-containing polymers suitable for use in molding or casting applications are formed by polymerization of an anhydride-containing precursor of the formula

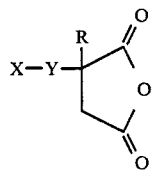

wherein
Y is a divalent hydrocarbon group or a divalent hydrocarbon group containing oxygen, sulfur, nitrogen, silicon, phosphorus or halogen atoms;
R is phenyl or $C_{1-10}$ alkyl; and
X is an oligomer or polymer-forming reactive moiety with reactive nitrogen-containing polyfunctional comonomers.

4 Claims, No Drawings

POLYMERS OF 3,3-DISUBSTITUTED-FURANDIONE COMPOUNDS

CROSS-REFERENCE TO RELATED APPLICATION

This is a continuation of application Ser. No. 214,611, filed Dec. 9, 1980, abandoned.

BACKGROUND OF THE INVENTION

The invention relates to new chemical compounds. In particular it relates to poly(imide)-containing polymeric materials made from 3,3-disubstituted-furandione derivatives which have been either homopolymerized or copolymerized.

In the prior art poly(imide)-containing polymers have been limited to those formed from an aromatic anhydride-containing compound containing a fused anhydride moiety, i.e., compounds having the anhydride functionality joined to an aromatic nucleus by covalent bonds to two adjacent carbons of a benzene ring. In contrast, the anhydride functionality in the precursors of the instant invented polymers is attached to the remainder of the molecule by one carbon of the cyclic five-membered anhydride moiety.

Furthermore, the imide ring moiety of the instant invented polymers has been found to be stabilized by reason of an alkyl or phenyl substituent attached at the same carbon atom through which the imide ring moiety joins the remainder of the polymer. The presence of this stabilizing alkyl or phenyl moiety has also been found to impart added stability to the imide ring moiety imparting to the invented polymers improved properties such as improved glass transition temperature and increased flexibility of objects formed from the invented polymers.

SUMMARY OF THE INVENTION

The invention comprises certain poly(imide)-containing polymers containing therein one or more structural moieties of the formula

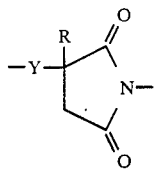

wherein:
Y is a divalent hydrocarbon group optionally containing oxygen, sulfur, nitrogen, silicon, phosphorus or halogen atoms; and
R is phenyl or $C_{1-10}$ alkyl.

DETAILED DESCRIPTION OF THE INVENTION

The anhydride-containing precursors used to form the polymers of this invention are of the formula

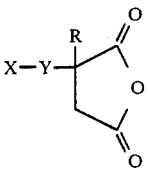

wherein:
X is $-NH_2$, $-C(O)Cl$, $-OH$ or $-CO_2R'$ where R' is hydrogen or R, and Y and R are as previously defined.

Synthesis of such precursors is illustrated by reference to the following schematic representation. They may be prepared by an initial Knovenagel condensation of an alkyl cyanoacetate with a carbonyl-containing compound of the formula

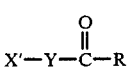

where X' is X or a precursor thereof, and X, Y and R are as previously defined.

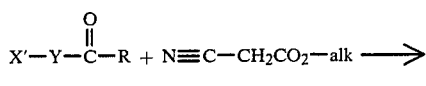

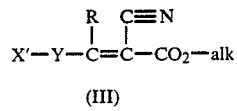

The radical, alk, represents lower alkyl, for example, methyl or ethyl.

The product, (III), is then reacted with an alkali metal cyanide to form the dicyanide (IV).

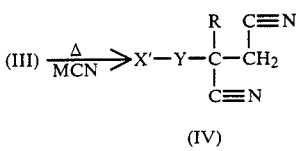

The dicyanide, (IV), is then acid hydrolyzed to the diacid, (V), which may be converted to the anhydride or converted directly to the poly(amide)imide.

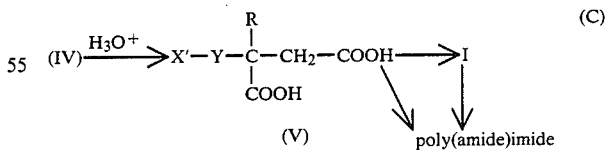

The condensation reaction, Step (A), is a known procedure and may be conducted in an inert organic solvent such as toluene, benzene or a chlorinated hydrocarbon. In general terms the two reactants are combined with the solvent in a reaction vessel which may be of ordinary design and construction such as one made of glass, steel, aluminum, etc. It is also advantageous to add to the solution a small amount of acetic acid and ammonium acetate.

The reactor and contents are then heated to reflux temperature and water formed by the reaction is removed as an azeotropic mixture. When the reaction is substantially complete the addition product is collected and purified if desired, for example by vacuum distillation.

The carbonyl-containing reactant II which may be reacted initially with an alkylcyanoacetate is further described in the following manner.

The substituent X' is a reactive moiety which is capable of reaction to form oligomeric and polymeric reaction products by reaction with an amine, isocyanate or carboxylate functionality, or a substituent that may be converted to such a reactive moiety. The term carboxylate as used herein includes carboxylic acids as well as esters and anhydrides produced therefrom. Illustratively, the substituent X' is selected from the group consisting of X, —C≡N, and —NO$_2$. Compounds wherein X is —C≡N may be converted into the corresponding carboxy compounds by acid hydrolysis, preferably as part of the same reaction utilized to convert the remaining cyanate moieties, i.e., reaction C. Compounds wherein X' is —NO$_2$ are converted to the corresponding amine-containing compound by hydrogenation of the nitro substituent. The conversion is preferably performed after hydrolysis of the compound's cyano functionality according to step C above. In this manner protection of the vulnerable amine so formed during the early stages of the synthesis is not necessary.

The substituent Y is, as previously explained, a divalent hydrocarbon group optionally containing oxygen, sulfur, nitrogen, silicon, phosphorus or halogen atoms. Its chemical structure otherwise is of little consequence to the operability of the invention. Illustratively, Y may be aliphatic, aromatic, cycloaliphatic, combination of aliphatic and/or cycloaliphatic and/or aromatic, bridged organic or inertly-substituted derivatives of the above.

Suitable divalent hydrocarbyl groups include:
$-\text{(CHB)}_n-$ where n is an integer from 1 to 20;
$-\text{(CHB)}_m\text{O}-\text{(CHB)}_p-$ where m and p each occurrence may be integers from 1 to 5; and
an aromatic or substituted aromatic divalent radical selected from:

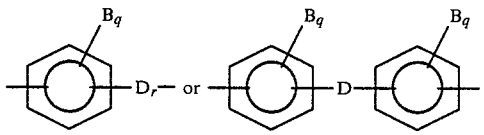

where B is $C_{1-4}$ alkyl, $C_{1-4}$ alkoxy, hydroxy, phenyl, nitro, organosilyl, alkyl, alkoxy, phosphino, phosphinyl or halo; D is sulfur, oxygen or alkylene; and q and r are independently each occurrence 0 or 1. By organosilyl are included triphenyl-, trialkyl- or trialkoxy-substituted silyl radicals having up to 12 carbons.

Preferred are compositions wherein Y is $C_{1-10}$ alkylene or phenylene. Most preferably Y is trimethylene.

The substituent R in the carbonyl-containing reactant is $C_{1-10}$ alkyl or phenyl. Preferably R is $C_{1-4}$ alkyl.

The nucleophilic addition of cyanide, step B, also a known procedure, is conducted in the following manner. The α-cyano-substituted acrylate reaction product of step A, purified if desired, is refluxed in a hydroxyl-containing polar solvent with a slight excess of an alkali metal cyanide.

A suitable solvent is water, a $C_{1-4}$ alkanol or glycol, or a mixture thereof. Preferably, in order to avoid degradation of the product by oxidation, oxygen is excluded from the reaction vessel, for example, by use of a nitrogen blanket.

Contrary to similar nucleophilic additions of cyanide discussed in the prior art, which teach use of a large excess of cyanide reactant, it has surprisingly been found that increased yields of the desired cyano-substituted product are obtained according to the instant process by utilizing only a small excess of cyanide reactant, preferably from about 1.0 to about 1.1 equivalents of cyanide for each equivalent of α-cyano-substituted acrylate.

When the reaction is substantially completed, heating is discontinued and the desired dicyano-substituted product is recovered from the alkali metal salt by-product.

In the final step, step C, the cyano groups of the compound are hydrolyzed to carboxy groups by known methods such as refluxing in concentrated acid. The acid-containing product is converted further to the anhydride by known procedures, most simply by merely heating.

It is seen that the anhydride-containing precursors of the invented polymers are difunctional. Present in the compounds are both a reactive functionality X, and an anhydride functionality. The precursor compounds may therefore be polymerized by reacting with a corresponding difunctional or polyfunctional compound capable of reacting with both X and the anhydride functionality.

When X is —NH$_2$, the precursor compounds may be homopolymerized. This is accomplished by heating, optionally in the presence of an effective amount of a polymerization catalyst such as manganese hypophosphite. Optionally, a difunctional comonomer containing both amine and carboxylate reactive moieties may also be copolymerized with the precursor compound as is well-known in the art. The amine-containing monomers may be produced according to the previously described synthesis, preferably after first protecting the amine functionality by conversion to the amide by contacting with acetic or other carboxylic acid.

Alternatively, where X is —OH, —C(O)Cl or —CO$_2$R', the above anhydride-containing precursors are copolymerized by reaction with a comonomer containing reactive nitrogen functionality according to well-known techniques in the art. Combinations of reactive nitrogen-containing polyfunctional comonomers may also be employed in mixture or sequentially to provide polymeric structures of two or more repeating structural units present in random or block sequence.

In the preferred embodiment, X is —C(O)Cl or —CO$_2$R'.

By reactive nitrogen-containing polyfunctional comonomer is meant a polyfunctional comonomer containing at least one amine or isocyanate functionality which may be reacted with the anhydride functionality of the invented compounds to form polyimide linkages according to known techniques. The remaining functionality of the comonomer is selected to form polymeric reaction products with X.

Suitable reactive nitrogen-containing comonomers depending on the identity of X may be selected from the group consisting of H₂N—Z—NH₂, H₂N—Z—COOH, OCN—Z—NCO and

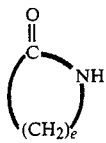

wherein e is an integer from 1 to 5, Z is a divalent hydrocarbon moiety of up to about 20 carbons selected from aliphatic; cycloaliphatic; aromatic; combination of aliphatic, cycloaliphatic, and/or aromatic; heterocyclic containing oxygen or nitrogen in addition to carbon; and bridged organic wherein the bridge is oxygen, sulfur, or oxy-, alkyl-, phenyl-, or alkoxy-substituted nitrogen, silicon, or phosphorus groups and combinations thereof.

Preferred reactive nitrogen-containing comonomers are diamines which may be coreacted with the previously identified preferred anhydrides wherein X is —C(O)Cl or —COOR' to form poly(amideimides).

The following examples illustrate the variety of anhydride-containing precursors as well as the variety of reactive nitrogen-containing comonomers that may be coreacted therewith to form the polyimide-containing polymers of the invention.

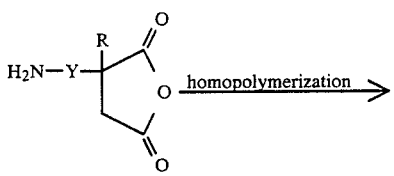 homopolymerization → (1)

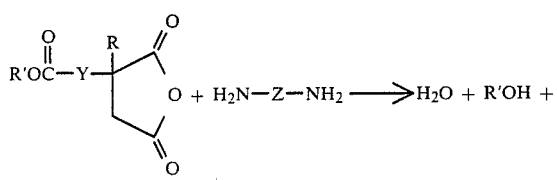

where R and Y are as previously defined and f is an integer indicating the number of repeating units in the polymer;

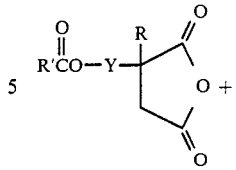 + (2)

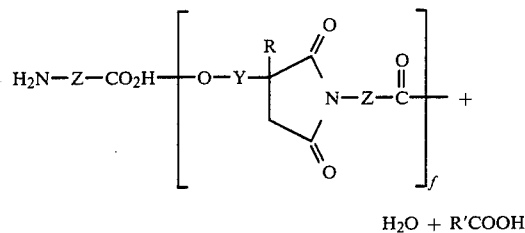

H₂O + R'COOH where Z, R, R', Y and f are as previously defined;

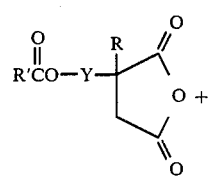 + (3)

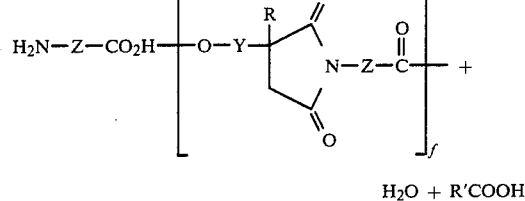 + R'COOH where R, R', Y, e and f are as previously defined;

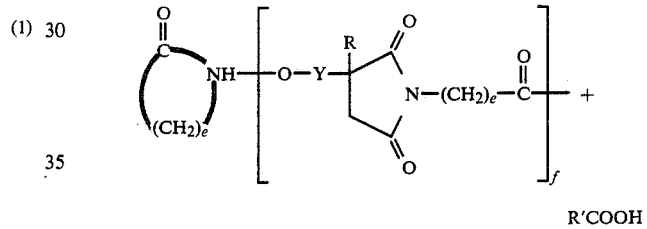 + H₂N—Z—NH₂ ⟶ H₂O + R'OH + (4)

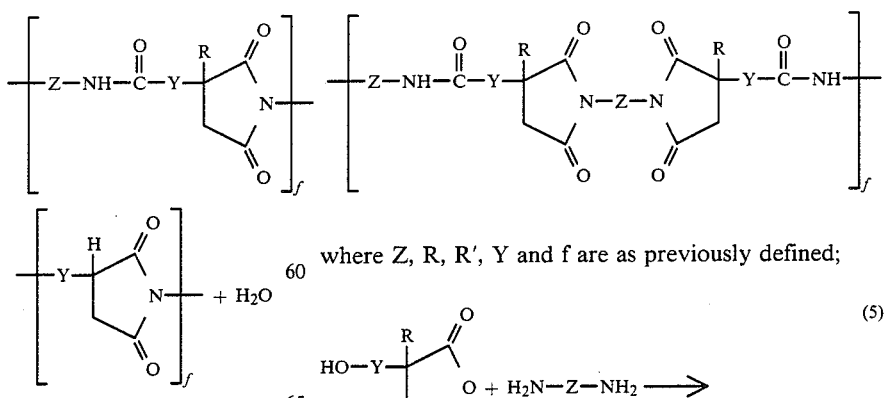

where Z, R, R', Y and f are as previously defined;

HO—Y... O + H₂N—Z—NH₂ ⟶ (5)

-continued

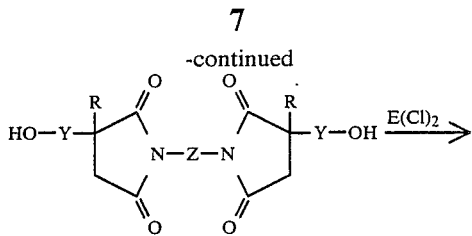

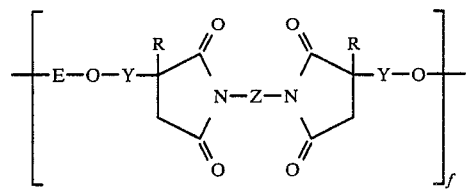

where R, R', Y, Z and f are as previously defined and E is selected from

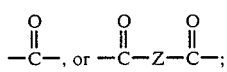

(6)

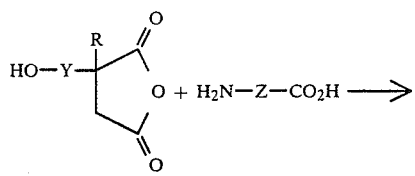

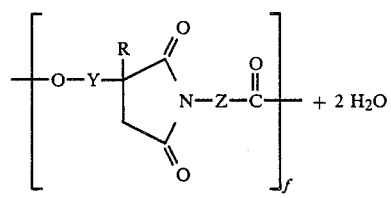

where R, R', Y, Z and f are as previously described;

(7)

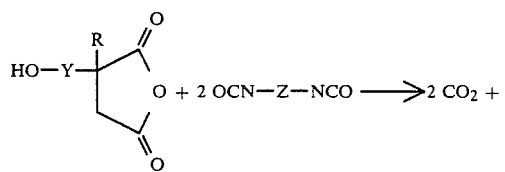

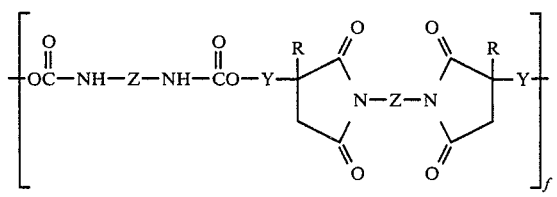

where R, R', Y, Z and f are as previously defined.

SPECIFIC EMBODIMENTS

The following examples are provided as further illustrative of the invention and are not to be construed as limiting.

EXAMPLE 1

A. Synthesis of ethyl-2,6-dicyano-3-methyl-2-hexenoate

A mixture of methyl 3-cyanopropyl ketone (55.5 g, 0.5 mole), ethyl cyanoacetate (56.5 g, 0.5 mole), acetic acid (6.0 g, 0.1 mole), ammonium acetate (3.85 g, 0.05 mole) and toluene (50 ml) was refluxed while azeotropically removing the water of reaction formed. After 10 hours the solution was vacuum distilled and a fraction (b.p. 145° C.–153° C., 0.5 torr) was collected. Total yield was 77.0 g or 74.7 percent. Analysis by infrared spectroscopy confirmed the product's identity as:

$NC-(CH_2)_3C(CH_3)=C(CN)CO_2C_2H_5$.

B. Conversion to 2-methyl-1,2,5-tricyanopentane

Example 1A was repeated to produce a large amount of the reaction product ethyl-2,6-dicyano-3-methyl-2-hexenoate. This product (557 g, 2.7 moles) was then combined with NaCN (139 g, 2.84 moles), water (1.8 liters) and ethanol (1.5 liters) and stirred under nitrogen atmosphere for about 2 hours. The mixture was then heated to reflux over an additional period of about 2 hours and then maintained at reflux for about 4 hours.

Heating was discontinued and the viscous reaction mixture worked up. First the sodium bicarbonate formed during the reaction was removed by filtration, and the remaining filtrate evaporated to about ⅓ of its original volume. The product was extracted with 3–500 ml quantities of methylene chloride. The methylene chloride extracts were then washed with saturated aqueous sodium chloride and dried over anhydrous $MgSO_4$. The methylene chloride was evaporated leaving a yellow-colored viscous liquid (418 g, 96 percent yield, b.p. 170° C.–180° C. at 0.5 torr). The product was identified by its infrared spectrum as essentially pure 2-methyl-1,2,5-tricyanopentane.

C. Conversion to 2-methylpentane-1,2,5-tricarboxylic acid

A portion of the 2-methyl-1,2,5-tricyanopentane produced in Example 1B (410 g, 2.5 moles) was combined with concentrated HCl (1.7 liters) and refluxed in a glass flask for 48 hours. The solution was then diluted with water (1.0 liter) and allowed to cool to room temperature. A solid precipitate resulted. The solid was washed with cold water to remove ammonium chloride and dried at 100° C. under vacuum for about 12 hours to yield highly pure 2-methylpentane-1,2,5-tricarboxylic acid.

D. Anhydride formation

A number of anhydride-containing reactive monomers were prepared from the 2-methylpentane-1,2,5-tricarboxylic acid produced in Example 1C above. Because ordinary techniques of anhydride formation well-known to the skilled artisan were employed, a detailed description of the reaction conditions will not be provided. The following Table I provides a list of the products formed and an abbreviated discussion of the synthetic methods employed. Unless otherwise stated the initial reactant was 2-methylpentane-1,2,5-tricarboxylic acid.

| Anhydride formed | Process conditions |
|---|---|
| (1) | |

| Anhydride formed | Process conditions |
|---|---|
| -continued | |
| (image) 4(tetrahydro-3-methyl-2,5-dioxo)furan butanoic acid | heating - 185° C.–200° C. |
| (2) (image) methyl 4(tetrahydro-3-methyl-2,5-dioxo)-furan butanate | Esterification by reflux with trimethyl orthoformate. Extraction with aqueous Na₂CO₃ to selectively extract dimethyl ester from trimethyl ester. Recovered dimethyl ester was heated to produce the anhydride. |
| (3) (image) 4(tetrahydro-3-methyl-2,5-dioxo)furan butanoyl chloride | Reacted with SOCl₂ in MeCl₂ at reflux. Product recovered by distillation b.p. 180° C. (0.5–1.0 torr). Converted to phenoxy derivative in D3a. |
| (3a) (image) phenyl 4(tetrahydro-3-methyl-2,5-dioxo)-furan butanoate | Previously prepared tetrahydro-3-methyl-2,5-dioxo-3-furan butanoyl chloride (D3) was treated with phenol and pyridine in MeCl₂ @ −15° C. Purified by distillation b.p. 200° C., 0.5 torr. |

E. Polymer Formation 1. 4(Tetrahydro-3-methyl-2,5-dioxo)furan butanoic acid (4.0 g, 0.02 mole) was combined in a polymer tube with bis(4-aminocyclohexyl)methane (4.15 g, 0.02 mole) and manganese hypophosphite catalyst (0.005 g). The tube was heated at 220° C. for about 30 minutes and then at 300° C. for an additional 30 minutes. A tough, white, opaque solid resulted having an inherent viscosity in N-methylpyrrolidinone (0.5 percent, 25° C.) of 0.64.

2. A dicarboxylic acid which also contained methyl ester functionality was formed by ring opening of the anhydride, 4(tetrahydro-3-methyl-2,5-dioxo)furan buta- noic acid. Accordingly, 20 g of the acid and 70 ml of methanol were combined and heated in a glass flask until a homogenous solution resulted. Bis(4-aminocyclohexyl)-methane (21.0 g) was added and the mixture cooled to room temperature. Upon dilution with ether, a fine white precipitate resulted which was identified as the diamine salt of the dicarboxylic acid. In the salt form the above polymeric precursor was easily weighed and handled. The above salt (8.80 g, 0.02 mole) was then combined with a further quantity of the acid, 4(tetrahydro-3-methyl-2,5-dioxo)furan butanoic acid (0.04 g, 1.0 mole percent based on salt), and manganese hypophosphite catalyst (0.05 g). The mixture was heated at 230° C. while flushing with nitrogen for about 1 hour, then at 250° C. for about 10 hours. The resulting white polymer could be shaped and pressed at 300° C. or solvent cast from dimethylacetamide into tough flexible films. Inherent viscosity in N-methylpyrrolidinone (0.5 percent, 25° C.) was 0.55.

Repeating structural units of the polymers prepared according to Example 1E correspond to one or both of the formulas

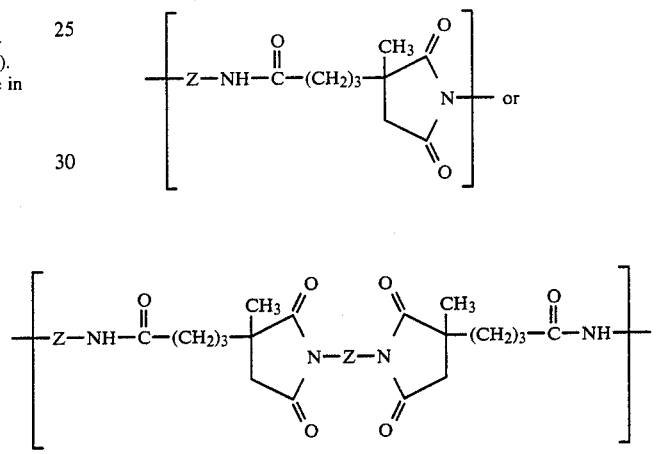

wherein Z is

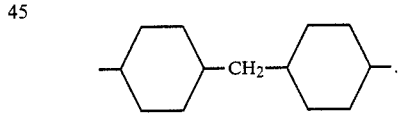

EXAMPLE 2

3-Methyl-3-(3-aminophenyl)tetrahydrofurandione

A. A solution consisting of m-nitroacetophenone (347.4 g, 95 percent purity, 2.0 moles), methylcyanoacetate (210.2 g, 2.08 moles), acetic acid (90 ml), benzene (600 ml) and ammonium acetate (4.0 g) was heated to reflux in a glass reactor equipped with a Dean-Stark apparatus to remove water. Additional 4.0-g portions of ammonium acetate were added at 2-hour intervals until a total amount of 20 g had been added. Heating was continued at reflux for a total of 24 hours.

Upon cooling, a light colored precipitate was observed. The solution was filtered and the amber colored filtrate heated on a water bath at 60° C. under vacuum (20 torr) until solvent was eliminated. A dark colored partially crystalline solid identified as having the formula

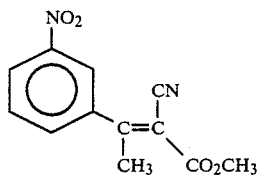

was obtained.

The resulting unpurified product was added to a 50 percent v/v ethanol-water solution in a glass reactor. Potassium cyanide (130 g, 2.0 moles), was added and the mixture heated to reflux for 10 minutes. The solution turned purple. Refluxing was continued for an additional hour and the solution was then cooled to 0° C. and acidified with concentrated HCl. Water (1.0 l) was added and the product extracted with methylene chloride, washed with water, dried over magnesium sulfate and recovered by solvent evaporation. Recrystallization from isopropanol gave 174.1 g, 35 percent yield of a compound identified by infrared spectroscopy as 1,2-dicyano-2-(3-nitrophenyl)propane,

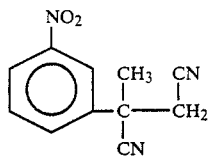

having a melting point of 117° C.–118° C.

B. The 1,2-dicyano-2-(3-nitrophenyl)propane (20.0 g, 0.093 mole) was suspended in 400 g of 83 percent $H_3PO_4$ and the mixture heated to 100° C.±5° for 24 hours. An amber solution gradually resulted which precipitated a white solid. Water washing and filtration resulted in recovery of 19.1 g, 83 percent yield of a light tan colored solid (m.p. 142° C.–143° C.). Analysis by infrared spectroscopy (IR) and nuclear magnetic resonance spectroscopy (NMR) identified the product as the diacid of the formula

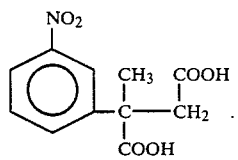

C. The nitro substituent of the above diacid was converted to the amine by catalytic hydrogenation. Accordingly, a suspension of the diacid (10.0 g, 0.040 mole) in p-dioxane (200 ml) was placed in a Parr shaker hydrogenator containing 1 g of 5 percent Pt on diatomaceous earth. Hydrogen at 60 psig was admitted and the mixture agitated for 48 hours. Filtration to separate catalyst left a clear solution which, upon evaporation, left a viscous colorless oil. Vacuum stripping of residual solvent gave a pure compound of the formula

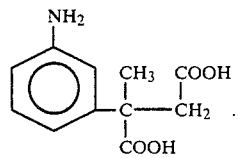

D. The above diacid may be easily converted to the anhydride by heating. However, to illustrate the equivalence of the diacid to the anhydride, a polyimide polymer was produced directly from the above diacid. Accordingly, the above product, α-methyl-α-(m-anilino)-succinic acid (6.0 g), was heated to 175° C. under nitrogen for 1 hour, the system was evacuated (3 torr) and the temperature increased to 275° C. for ½ hour. A viscous melt was observed. Heating was continued for 2 hours to allow for complete homopolymerization. The system was then cooled and opened.

The resulting polymer was identified as having the formula

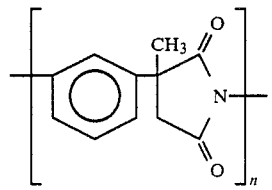

Inherent viscosity (0.5 percent in N-methyl pyrrolidone, 25° C.) was 0.58. Torsional braid analysis indicated a Tg of 180° C. This glass transition temperature for the polymer is much lower than glass transition temperatures of known polyimide polymers and is thought to be due to the increased flexibility due to the aliphatic backbone of the polymer and the presence of the methyl substituent in the 2,5-pyrrolidinedione ring system. The polymers are therefore more suitable for molding applications than previously employed polyimides.

What is claimed is:

1. A poly(imide)-containing polymer consisting essentially of recurring units of the formula

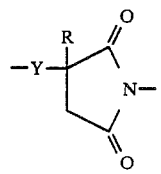

wherein:
Y is a divalent hydrocarbon group or a divalent hydrocarbon group containing oxygen, sulfur, nitrogen, silicon, phosphorus, or halogen atoms; and
R is phenyl or $C_{1-10}$ alkyl.

2. A poly(imide)-containing polymer according to claim 1 wherein the poly(imide)-containing polymer is a homopolymer of:

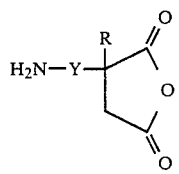

where:
Y is a divalent hydrocarbon group or a divalent hydrocarbon group containing oxygen, sulfur, nitrogen, silicon, phosphorus or halogen atoms; and
R is phenyl or $C_{1-10}$ alkyl.

3. A poly(imide)-containing polymer according to claim 2 wherein Y is $C_{1-10}$ alkylene or phenylene.

4. A poly(imide)-containing polymer according to claim 3 wherein R is $C_{1-4}$ alkyl.

* * * * *

UNITED STATES PATENT AND TRADEMARK OFFICE
CERTIFICATE OF CORRECTION

PATENT NO. : 4,525,577

DATED : June 25, 1985

INVENTOR(S) : Edmund P. Woo & Michael J. Mullins

It is certified that error appears in the above-identified patent and that said Letters Patent is hereby corrected as shown below:

Column 5, line 58, "H" should read -- R --.

Signed and Sealed this

Tenth Day of December 1985

[SEAL]

Attest:

DONALD J. QUIGG

Attesting Officer

Commissioner of Patents and Trademarks